United States Patent [19]

Bernstein et al.

[11] 4,108,890

[45] Aug. 22, 1978

[54] NITRO OR AMINO PHENYLENEBIS(CARBONYLIMINO)-DINAPHTHALENETRISULFONIC COMPOUNDS AS COMPLEMENT INHIBITORS

[75] Inventors: Seymour Bernstein, New City, N.Y.; Robert Herman Lenhard, Paramus, N.J.; Ransom Brown Conrow, Pearl River, N.Y.

[73] Assignee: American Cyanamid Company, Stamford, Conn.

[21] Appl. No.: 813,131

[22] Filed: Jul. 5, 1977

Related U.S. Application Data

[62] Division of Ser. No. 684,690, May 10, 1976, Pat. No. 4,051,176.

[51] Int. Cl.$^2$ ............................................. C07C 143/52
[52] U.S. Cl. ................................................ 260/507 R
[58] Field of Search ............................. 260/506, 507 R

[56] References Cited

U.S. PATENT DOCUMENTS

| | | | |
|---|---|---|---|
| 4,046,805 | 9/1977 | Bernstein et al. | 260/506 |
| 4,051,176 | 9/1977 | Bernstein et al. | 260/506 |

*Primary Examiner*—Nicky Chan
*Attorney, Agent, or Firm*—Jack W. Richards

[57] ABSTRACT m-Phenylenebis(carbonylimino)dinaphthalenetrisulfonic acids and salts useful as complement inhibitors.

7 Claims, No Drawings

NITRO OR AMINO PHENYLENEBIS(CARBONYLIMINO)DINAPHTHALENETRISULFONIC COMPOUNDS AS COMPLEMENT INHIBITORS

This is a division of application Ser. No. 684,690 filed May 10, 1976, now U.S. Pat. No. 4,051,176.

BACKGROUND OF THE INVENTION

The present invention resides in the concept of certain m-phenylenebis(carbonylimino)dinaphthalenetrisulfonic acids and salts and their use as inhibitors of the complement system of warm-blooded animals.

The term "complement" refers to a complex group of proteins in body fluids that, working together with antibodies or other factors, play an important role as mediators of immune, allergic, immunochemical and/or immunopathological reactions. The reactions in which complement participates takes place in blood serum or in other body fluids, and hence are considered to be humoral reactions.

With regard to human blood, there are at present more than 11 proteins in the complement system. These complement proteins are designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its role in body processes can be found in, for example, Bull. World Health Org. 39, 935–938 (1968); Scientific American, 229, (No. 5), 54–66 (1973); Medical World News, Oct. 11, 1974, pp. 53–58; 64–66; Harvey Lectures, 66, 75–104 (1972); The New England Journal of Medicine, 287, 489–495, 545–549, 592–596, 642–646 (1972); The Johns Hopkins Med. J. 128, 57–74 (1971); and Federation Proceedings, 32, 134–137 (1973).

The complement system can be considered to consist of three subsystems: (1) a recognition unit (C1q) which enables it to combine with antibody molecules that have detected a foreign invader; (2) an activation unit (C1r, C1s, C2, C4, C3), which prepares a site on the neighboring membrane; and (3) an attack unit (C5, C6, C7, C8 and C9) which creates a "hole" in the membrane. The membrane attack unit is nonspecific; it destroys invaders only because it is generated in their neighborhood. In order to minimize damaage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is therefore a double-edged sword.

Activation of the complement system also accelerates blood clotting. This action comes about by way of the complement-mediated release of a clotting factor from platelets. The biologically active complement fragments and complexes can become involved in reactions that damage the host's cells, and these pathogenic reactions can result in the development of immune-complex diseases. For example, in some forms of nephritis complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease, in which the disease symptoms are caused by pathological efforts of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membrane. Thus, while complement constitutes a part of the body's defense mechanism against infection, it also results in inflammation and tissue damage in the immunopathological process. The nature of certain of the complement proteins, suggestions regarding the mode of complement binding to biological membranes and the manner in which complement effects membrane damage are discussed in Annual Review of Biochemistry, 38, 389 (1969).

A variety of substances have been disclosed as inhibiting the complement system, i.e., as complement inhibitors. For example, the compounds 3,3'-ureylenebis[6-(2-amino-8-hydroxy-6-sulfo-1-naphthylazo)benzenesulfonic acid] tetrasodium salt (chlorazol fast pink), heparin and a sulphated dextran have been reported to have an anticomplementary effect, British Journal of Experimental Pathology, 33, 327–339 (1952). The compound 8,8'-[ureylenebis[m-phenylenecarbonylimino(4-methyl-m-phenylene)carbonylimino]]di-1,3,5-naphthalenetrisulfonic acid, hexasodium salt (Suramin Sodium) is described as a competitive inhibitor of the complement system, Clin. Exp. Immunol., 10, 127–138 (1972). German Patent No. 2,254,893 or South African Patent No. 727,923 discloses certain 1-(diphenylmethyl)-4-(phenylallyl)piperazines useful as complement inhibitors. U.S. Pat. No. 3,897,434 discloses certain pyrazolo[1,5-c]quinazolin-5(6H)ones useful as complement inhibitors. Other chemical compounds having complement inhibiting activity are disclosed in, for example, Journal of Medicinal Chemistry, 12, 415–419, 902–905, 1053–1056 (1969); Canadian Journal of Biochemistry, 47, 547–552 (1969); The Journal of Immunology, 93, 629–640 (1964); The Journal of Immunology, 104, 279–288 (1970); The Journal of Immunology, 106, 241–245 (1971); and The Journal of Immunology, 111, 1061–1066 (1973).

It has been reported that the known complement inhibitors epsilon-aminocaproic acid, Suramin Sodium, and tranexamic acid have been used with success in the treatment of hereditary angioneurotic edema, a disease state resulting from an inherited deficiency or lack of function of the serum inhibitor of the activated first component of complement (C1 inhibitor), The New England Journal of Medicine, 286, 808–812 (1972); Allergol, Et. Immunopath, II, 163–168 (1974); and J. Allergy Clin. Immunol., 53, No. 5, 298–302 (1974).

SUMMARY OF THE INVENTION

It has now been discovered that certain m-phenylenebis(carbonylimino)dinaphthalenetrisulfonic compounds interact with the complement reaction sequence, thereby inhibiting complement activity in body fluids.

This invention is particularly concerned with compounds having complement inhibiting activity of the general formula (I):

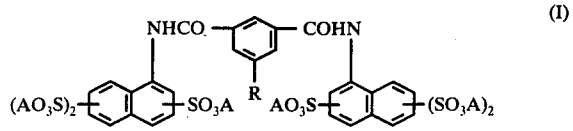

wherein R is selected from the group $NO_2$; $NH_2$;

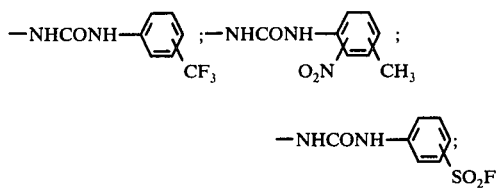

and A is hydrogen, alkaline earth or alkali metal, with the proviso that each A is identical in the same compound. Preferably, A is sodium or potassium.

Of particular interest in the above general formula (I) are the group of compounds wherein A is Na (sodium) and, within this group, those compounds of most interest are those of general formulae (II) and (III):

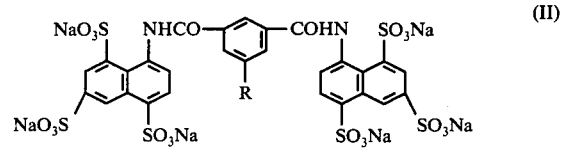

wherein R is selected from the group -$NO_2$; -$NH_2$;

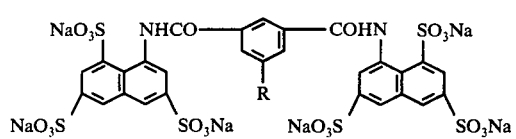

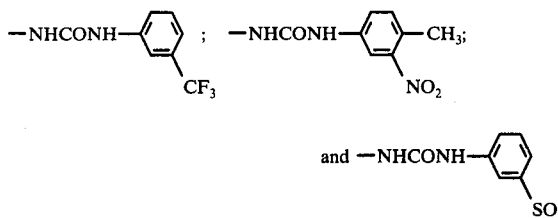

Representative compounds encompassed within this invention, formula (II), include, for example, 8,8'-[(5-nitro-1,3-phenylene)bis(carbonylimini)]di-1,3,5-naphthalenetrisulfonic acid, hexasodium salt; 8,8'-[(5-amino-1,3-phenylene)bis (carbonylimino)]di-1,3,5-naphthaleentrisulfonic acid, hexasodium salt; 8,8'-{{5-[3-(α,α,α-trifluoro-m-tolyl)ureido]-1,3-phenylene}bis(carbonylimino)}di-1,3,5-naphthalenetrisulfonic acid, hexasosium salt; 8,8'-{{5-[3-(3-nitro-p-tolyl) ureido]-1,3-phenylene}bis(carbonylimino)}di-1,3,5-naphthalenetrisulfonic acid, hexasodium salt; and 8,8'-{{5-{3-[m-fluorosulfonyl)phenyl]ureido}-1,3-phenylene}bis(carbonylimino)}di-1, 3,5-naphthalenetrisulfonic acid, hexasodium salt.

Representative compounds encompassed within this invention, formula (III), include, for example, 8,8'-[(5-nitro-1,3-phenylene)bis(carbonylimino)]di-1,3,6-naphthalenetrisulfonic acid, hexasodium salt; 8,8'-[(5-amino-1,3-phenylene)bis(carbonylimino)]di-1,3,6-naphthalenetrisulfonic acid, hexasodium salt; 8,8'-{{5-[3-(α,α,α-trifluoro-m-tolyl)ureido]-1,3-phenylene}bis(carbonylimino}di-1,3,6-naphthalenetrisulfonic acid, hexasodium salt; 8,8'-{{5-[3-(3-nitro-p-tolyl) ureido]-1,3-phenylene}bis(carbonylimino)}di-1,3,6-naphthalenetrisulfonic acid, hexasodium salt; and 8,8'-{{5-{3-[m-(fluorosulfonyl)phenyl]ureido}-1,3-phenylene}bis(carbonylimino}di-1,3,6-naphthalenetrisulfonic acid, hexasodium salt.

The closest known compounds disclosed as having anticomplementary effect are the compounds 3,3'-ureylenebis[6-(2-amino-8-hydroxy-6-sulfo-1-naphthylazo)benzenesulfonic acid] tetrasodium salt (chlorazol fast pink), *British Journal of Experimental Pathology*, 33, 327–339 (1952); 8,8'-[ureylenebis[m-phenylenecarbonylimino(4-methyl-m-phenylene)carbonylimino]]di-1,3,5-naphthalenesulfonic acid, hexasodium salt (Suramin Sodium), *Clin. Exp. Immunol.* 10, 127–138 (1972); m-[m-(p-nitrophenylureido)phenoxypropoxy]benzamidine, *Immunol.*, 26, 819–829 (1974); and those compounds disclosed in the *Journal of Medicinal Chemistry*, supra. Other known compounds are those disclosed in *Biochemical Journal*, 42, 109–116 (1948); *Annales De L'Institut Pasteur*, 38, 6: 82–114 (1924); *Journal of the Chemical Society*, Part III, 3739–3744 (1956); *Journal of the Chemical Society*, Part III, 3068–3097 (1927); *Biochemical Journal*, 47, 149–170 (1950).

The compounds of this invention may be prepared, for example, according to the following illustrative general procedure: Treatment of 8-amino-1,8,5(or 6)-naphthalenetrisulfonic acid, trisodium salt with 5-nitroisophthaloyl chloride provides the 8,8'-[5-nitro-1,3-phenylene)bis(carbonylimino)]di-1,3,5-(or 6)-naphthalenetrisulfonic acid, hexasodium salts. Reduction of the nitro-group gives the corresponding 5-amino compounds. Reaction of the latter with aromatic isocyanates provide the ureides of the invention. Acidification produces the free acid.

This invention is also concerned with a method of inhibiting the complement system in a body fluid, such as blood serum, which comprises subjecting body fluid complement to the action of an effective complement inhibiting the amount of a compound encompassed within formulae (I), (II) and (III) hereinabove. The method of use aspect of this invention is further concerned with a method of inhibiting the complement system in a warm-blooded animal which comprises internally administering to said animal an effective complement inhibiting amount of a compound encompassed within formulae (I), (II) and (III) hereinabove. Body fluid can include blood, plasma, serum, synovial sluid, cerebrospinal fluid, or pathological accumulations of fluid such as pleural effusion, etc, containing complement.

The compounds of the present invention find utility as complement inhibitors in body fluid and as such may be used to ameliorate or prevent those pathological reactions requiring the function of complement and in the therapeutic treatment of warm-blooded animals having diseases such as rheumatoid arthritis, systemic lupus erythematosus, certain kinds of glomerulonephritis, certain kinds of auto-allergic hemolytic anemia, certain kinds of platelet disorders and certain kinds of vasculitis. The compounds herein may also be used in the therapeutic treatment of warm-blooded animals having non-immunologic diseases such as paroxysmal nosturnal hemoglobinuria, hereditary angioneurotic edema (treated with Suramin, etc.) and inflammatory states induced by the action of bacterial of lysosomal enzymes on the appropriate complement component as for example, inflammation following coronary occlusion. They may also be useful in the treatment of transplant rejection and as blood culture or transport mediums.

DETAILED DESCRIPTION OF THE INVENTION

The following examples will serve to illustrate the invention in more detail.

EXAMPLE 1

8,8'-[(5-Nitro-1,3-phenylene)bis-(carbonylimino)]di-1,3,6-naphthalenetrisulfonic acid, hexasodium salt A mixture of 10.0 g of 5-nitroisophthalic acid, 50 ml of thionyl chloride and 0.2 ml of dimethylformamide is refluxed with stirring for 2½ hours. The solution is allowed to stand 48 hours at room temperature then is evaporated to an oil in vacuo. The evaporation step is repeated several times with cyclohexane and then toluene. Finally hexane is added and partial evaporation produced crystals. The mixture is cooled, then filtered. The crystals are washed with cold hexane to give 5-nitroisophthaloyl chloride.

To a solution of 25.5 g of 8-amino-1,3,6-naphthalenetrisulfonic acid, trisodium salt is 100 ml of water and 60 ml of N sodium hydroxide at room temperature is added 8.13 g of 5-nitroisophthaloyl chloride with about 25 ml of ether. The mixture is shaken briefly and a second 60 ml portion of N sodium hydroxide is added. The mixture is shaken for 5 minutes and a third 60 ml portion of N sodium hydroxide is added. The mixture is shaken for 15 minutes and a 1.0 portion of the acid chloride is added with a few ml of ether, shaking is resumed for an additional 45 minutes then the mixture is acidified with 5 ml of concentrated hydrochloric acid and extracted with four 150 ml portions of ether. The aqueous solution is neutralized and is concentrated to about 50 ml in vacuo at 55° C. The remaining liquid is allowed to stand at room temperature for 48 hours and forms a solid which is diluted with 125 ml of 80% ethyl alcohol and triturated. The material is filtered and washed with 80% ethyl alcohol, absolute ethanol and ether, then dried at 120° C for a few hours. The product is then dissolved in 60 ml of water, heated on the steam bath and diluted with 300 ml of absolute ethanol. The material is filtered and washed and the final product is then dried at 120° C overnight to give 8,8'-[(5-nitro-1,3-phenylene)bis(carbonylimino)]di-1,3,6-naphthalenetrisulfonic acid, hexasodium salt.

EXAMPLE 2

8,8'-[Amino-m-phenylene)bis(carbonylimino)]di-1,3,6-naphthalenetrisulfonic acid, hexasodium salt A mixture of 23.0 g of 8,8'-[(5-nitro-1,3-phenylene)bis(carbonylimino)]di-1,3,6-naphthalenetrisulfonic acid, hexasodium salt, 150 ml of water and 2.3 g of 10% palladium catalyst on carbon is hydrogenated at room temperature for 5 hours at an average pressure of 43 lbs, then is filtered through diatomaceous earth and washed with water. The filtrate is then concentrated to a small volume in vacuo, absolute ethanol is added and the resulting oil is triturated until a solid is formed. This material is filtered and washed with absolute ethanol followed by ether. The product is then oven dried at 120° C to give 8,8'-[(5-amino-1,3-phenylene)bis(carbonylimino)]di-1,3,6-naphthalenetrisulfonic acid, hexasodium salt.

EXAMPLE 3

8,8'-{{5-[3-(α,α,α-Trifluoro-m-tolyl)ureido]-1,3-phenylene}bis(carbonylimino)}di-1,3,6-naphthalenetrisulfonic acid, hexasodium salt To a stirred solution of 4.0 g of 8,8'-[(5-amino-1,3-phenylene)bis(carbonylimino)]di-1,3,6-naphthalenetrisulfonic acid, hexasodium salt in 50 ml of water is added 4.0 ml of 3-trifluoromethylphenyl isocyanate. Stirring is continued for 6 hours at room temperature then the resulting mixture is heated to 95° C, is filtered through diatomaceous earth and washed with 50 ml of hot water. The hot filtrate is salted with 55 g of sodium acetate trihydrate and after standing for 40 hours is diluted with 700 ml of anhydrous ethanol. The precipitate is filtered and washed with absolute ethanol and ether. The product is then boiled and triturated with 100 ml of absolute ethanol, cooled to room temperature and is filtered and washed with absolute ethanol followed by ether to give 8,8'-{{5-[3-(α,α,α-trifluoro-m-tolyl)ureido]-1,3-phenylene}bis(carbonylimino)}di-1,3,6-naphthalenetrisulfonic acid, hexasodium salt.

EXAMPLE 4

8,8'-{{5-[3-(3-Nitro-p-tolyl)ureido]-1,3-phenylene}bis(carbonylimino)}di-1,3,6-naphthalenetrisulfonic acid, hexasodium salt To a stirred solution of 4.0 g of 8,8'-[(5-amino-1,3-phenylene)bis(carbonylimino)]di-1,3,6-naphthalenetrisulfonic acid, hexasodium dalt in 60 ml of water is added 4.0 g of pulverized 4-methyl-3-nitrophenylisocyanate. Stirring is continued for 6 hours at room temperature, the resulting mixture is heated to about 95° C, is filtered through diatomaceous earth and washed with 50 ml of hot water. The filtrate is diluted with 600 ml of absolute ethanol while heating on a steam bath. The solution is filtered after standing at room temperature overnight and the precipitate is washed with absolute ethanol followed by ether. The product is then oven dried at 120° C overnight to give 8,8'-{{5-[3-(3-nitro-p-tolyl)-ureido]-1,3-phenylene}bis(carbonylimino)}di-1,3,6-naphthalenetrisulfonic acid, hexasodium salt.

EXAMPLE 5

8,8'-{{5-{3-[m-(Fluorosulfonyl)phenyl]ureido}-1,3-phenylene}bis(carbonylimino)}-di-1,3,6-naphthalenetrisulfonic acid, hexasodium salt To a stirred solution of 3.0 g of 8,8'-[(5-amino-m-phenylene)bis(carbonylimino)]di-1,3,6-naphthalenetrisulfonic acid, hexasodium salt in 45 ml of water is added 3.0 g of m-fluorosulfonylphenylisocyanate. Stirring is continued for 6 hours at room temperature, the resulting mixture is heated to about 95° C and is filtered through diatomaceous earth. The filter pad is washed with 40 ml of hot water and the filtrate is diluted with 500 ml of anhydrous ethanol while heating in a steam bath. The solution is filtered after standing at room temperature for 72 hours and the precipitate is washed with absolute ethanol followed by ether to give 8,8'-{{5-{3-[m-(fluorosulfonyl)phenyl]ureido}-1,3-phenylene}bis(carbonylimino)}di-1,3,6-naphthalenetrisulfonic acid, hexasodium salt.

EXAMPLE 6

8,8'-[(5-Nitro-1,3-phenylene)bis(carbonylimino)]di-1,3,5-naphthalenetrisulfonic acid, hexasodium salt In a manner similar to that of Example 1, the compound 8,8'-[(5-Nitro-1,3-phenylene)bis(carbonylimino)]di-1,3,5-naphthalenetrisulfonic acid, hexasodium salt can be prepared from 5-nitroisophthaloyl chloride and 8-amino-1,3,5-naphthalenesulfonic acid, trisodium salt.

EXAMPLE 7

8,8'-[(5-Amino-1,3-phenylene)bis(carbonylimino)]di-1,3,5-naphthalenetrisulfonic acid, hexasodium salt In a manner similar to that of Example 2, the compound 8,8'-[(5-amino-1,3-phenylene)bis(carbonylimino)]di-1,3,6-naphthalenetrisulfonic acid, hexasodium salt can be prepared from 8,8'-[(5-nitro-1,3-phenylene)bis(carbonylimino)]di-1,3,5-naphthalenetrisulfonic acid, hexasodium salt.

EXAMPLE 8

8,8'-{{5-[3-(α,α,α-Trifluoro-m-tolyl)ureido]-1,3-phenylene}bis(carbonylimino)}di-1,3,5-naphthalenetrisulfonic acid, hexasodium salt In a manner similar to that of Example 3, the compound 8,8'-{{5-[3-(α,α,α-trifluoro-m-tolyl)ureido]-1,3-phenylene}bis(carbonylimino)}di-1,3,5-naphthalenetrisulfonic acid, hexasodium salt can be prepared from 8,8'-[(5-amino-1,3-phenylene)bis(carbonylimino)]-1,3,5-naphthalenetrisulfonic acid, hexasodium salt and 3-trifluoromethylphenyl isocyanate.

EXAMPLE 9

8,8'-{{5-[3-(3-Nitro-p-tolyl)ureido]-1,3-phenylene}bis(carbonylimino)}di-1,3,5-naphthalenetrisulfonic acid, hexasodium salt In a manner similar to that of Example 4, the compound 8,8'-{{5-[3-(3-nitro-p-tolyl)ureido]-1,3-phenylene}bis(carbonylimino)}di-1,3,5-naphthalenetrisulfonic acid, hexasodium salt can be prepared from 8,8'-[(5-amino-1,3-phenylene)bis(carbonylimino)]di-1,3,5-naphthalenetrisulfonic acid, hexasodium salt and 4-methyl-3-nitrophenyl isocyanate.

EXAMPLE 10

8,8'-{{5-{3-[m-(Fluorosulfonyl)phenyl]ureido}-1,3-phenylene}bis(carbonylimino)}di-1,3,5-naphthalenetrisulfonic acid, hexasodium salt In a manner similar to that of Example 5, the compound 8,8'-{{5-{3-[m-(fluorosulfonyl)phenyl]ureido}-1,3-phenylene}bis(carbonylimino)}di-1,3,5-naphthalenetrisulfonic acid, hexasodium salt can be prepared from 8,8'-[(5-amino-1,3-phenylene)bis(carbonylimino)]-di-1,3,5-naphthalenetrisulfonic acid, hexasodium salt and m-fluorosulfonylphenylisocyanate.

EXAMPLE 11

Preparation of Compressed Tablet

| | mg./tablet |
|---|---|
| Active Compound | 0.5–500 |
| Dibasic Calcium Phosphate NF | qs |
| Starch USP | 40 |
| Modified Starch | 10 |
| Magnesium Stearate USP | 1–5 |

EXAMPLE 12

Preparation of Compressed Tablet-Sustained Action

| | mg./tablet |
|---|---|
| 8,8'-{{5-Amino-m-phenylene}bis-(carbonylimino)}-di-1,3,5 or 6-napthalenetrisulfonic acid, hexasodium salt aluminum lake,* micronized | 0.5–500 as acid equivalent |
| Dibasic Calcium Phosphate NF | qs |
| Starch USP | 20 |
| Magnesium Stearate USP | 1–10 |

*Complement inhibitor plus aluminum sulfate yields aluminum complement inhibitor. Complement inhibitor content in aluminum lake ranges from 5 to 30%.

EXAMPLE 13

Preparation of Hard Shell Capsule

| | mg./capsule |
|---|---|
| 8,8'-{{5-[3-(α,α,α-Trifluoro-m-tolyl)-ureido]-1,3-phenylene}bis(carbonylimino)}di-1,3,5 or 6-naphthalenetrisulfonic acid, hexasodium salt | 0.5–500 |
| Lactose, Spray Dried | qs |
| Magnesium Stearate | 1–10 |

EXAMPLE 14

Preparation of Oral Liquid (Syrup)

| | % W/V |
|---|---|
| 8,8'-{{5-[3-(3-Nitro-p-tolyl)ureido]-1,3-phenylene}bis(carbonylimino)}di-1,3,5 or 6-naphthalenetrisulfonic acid, hexasodium salt | 0.05–5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 15

Preparation of Oral Liquid (Elixir)

| | % W/V |
|---|---|
| 8,8'-{{5-{3-[m-(Fluorosulfonyl)phenyl]ureido}-1,3-phenylene}-bis(carbonylimino)}di-1,3,5 or 6-naphthalenetrisulfonic acid, hexasodium salt | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 16

Preparation of Oral Suspension (Syrup)

| | % W/V |
|---|---|
| 8,8'-[(5-Nitro-1,3-phenylene)bis- | 0.05–5 |

-continued
Preparation of Oral Suspension (Syrup)

| | % W/V |
|---|---|
| (carbonylimino)]di-1,3,5 or 6-naphthalenetrisulfonic acid, hexasodium salt | (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 17

Preparation of Injection Solution

| | % W/V |
|---|---|
| 8,8'-[(5-Amino-1,3-phenylene)bis-(carbonylimino)]di-1,3,5 or 6-naphthalenetrisulfonic acid, hexasodium salt | 0.05–5 |
| Benzyl Alcohol N.F. | 0.09 |
| Water for Injection | 100.0 |

EXAMPLE 18

Preparation of Injectable Oil

| | % W/V |
|---|---|
| 8,8'- 5-[3-($\alpha,\alpha,\alpha$-Trifluoro-m-tolyl)ureido]-1,3-phenylene bis-(carbonylimino) di-1,3,5 or 6-naphthalenetrisulfonic acid, hexasodium salt | 0.05–5 |
| Benzyl Alcohol | 1.5 |
| Sesame Oil qs ad | 100.0 |

EXAMPLE 19

Preparation of Injectable Depo Suspension

| | % W/V |
|---|---|
| 8,8'- 5-[3-Nitro-p-tolyl)ureido]-1,3-phenylene bis(carbonylimino)-di-1,3,5 or 6-naphthalenetrisulfonic acid, hexasodium salt as aluminum lake, micronized | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to pH 6 – 8 | qs |
| Water for Injection qs ad | 100.0 |

EXAMPLE 20

Preparation of Intra-Articular Preparation

| | |
|---|---|
| 8,8'-5-[3-($\alpha,\alpha,\alpha$-Trifluoro-m-tolyl)ureido]-1,3-phenylenebis(carbonylimino)di-1,3,5(6)-naphthalenetrisulfonic acid hexasodium salt | 2–20 mg |
| NaCl (physiological saline) | 0.9% |
| Benzyl Alcohol | 0.9% |
| *Sodium Carboxymethylcellulose (NaCMe) | 1–5% |
| pH adjusted to 5.0–7.5 | |
| Water for injection qs to | 100% |

*Increasing the NaCMe forms a syrupy solution of water-soluble compounds.

The compounds of this invention may be administered internally, e.g., orally or parenterally, such as intra-articularly, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg./kg./day, or every 6 hours for more rapidly excreted salts, may be used. For intra-articular use for large joints such as the knee, from about 2 to about 20 mg./joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg./kg. to about 100 mg./kg. of body weight of animal per day. The usual daily dosage for a 70 kg. subject may vary from about 350 mg. to about 3.5 g. Unit doses of the compound can contain from about 0.5 mg. to about 500 mg.

In therapeutic use the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety for forms depending on the form of preparation desired for administration, i.e., oral or parenteral. The compounds can be used in compositions as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, tha tablet or pill can comprise an inner dosgae, an outer dosage component, the latter being in the form of an envelope over the former. The two components can be separated by an enteric layer which serves to resist disintegration in the stomach and permits the inner component to pass intact into the suodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together wirh known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form as described herein refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powders packets, granules, wafers, cachets, teaspoonfuls, dropperfuls, ampules, vials, segregated multiples of any of the foregoing and other forms as herein described.

The complement inhibiting activity of representative compounds of this invention has been demonstrated by one or more of the following identified tests: (i) Test, Code 026 (C1 inhibitor). This test measures the ability of activated human C1 to destroy fluid phase human C2 in the presence of C4 and appropriate dilutions of the test compound. An active inhibitor protects C2 from C1 and C4; (ii) Test, Code 035 (C3-C9 inhibitor) — This determines the ability of the late components of human complement (C3-C9) to lyse EAC 142 in the presence of appropriate dilutions of the test compound. An active inhibitor protects EAC 142 from lysis by human C3-C9; (iii) Test, Code 036 (C-Shunt inhibitor) — In this test human erythrocytes rendered fragile are lysed in autologous serum via the shunt pathway activated by cobra venom factor in the presence of appropriate solutions of the test compound. Inhibition of the shunt pathway results in failure of lysis; (iv) Forssman Vasculitis Test — Here, the well known complement dependent lesion, Forssman vasculitis, is produced in guinea pigs by intradermal injection of rabbit anti-Forssman antiserum. The lesion is measured in terms of diameter, edema and hemorrhage and the extent to which a combined index of these is inhibited by prior intraperitoneal injection of the test compound at 200 mg./kg. is then reported, unless otherwise stated; (v) Forssman Shock Test — Lethal shock is produced in guinea pigs by an i.v. injection of anti-Forssman antiserum and the harmonic mean death time of treated guinea pigs is compared with that of simultaneous controls; (vi) Complement Level Reduction Test — In this test, the above dosed guinea pigs, or others, are bled for serum and the complement level is determined in undiluted serum by the capillary tube method of U.S. Pat. No. 3,876,376 and compared to undosed control guinea pigs; and (vii) Cap 50 Test — Here, appropriate amounts of the test compound are added to a pool of guinea pig serum in vitro, after which the undiluted serum capillary tube assay referred to above is run. The concentration of compound inhibiting 50% is reported.

Table I shows that representative compounds of the invention possess complement inhibitory activity.

TABLE I

| Compound | Biological Activities | |
|---|---|---|
| | 026* | 035 |
| 8,8'-[(5-nitro-1,3-phenylene)bis(carbonyl-imino)]di-1,3,6-naphthalenetrisulfonic acid, hexasodium salt | +4** | Neg. |
| 8,8'-[(5-amino-1,3-phenylene)bis(carbonyl-imino)]di-1,3,6-naphthalenetrisulfonic acid, hexasodium salt | +4 | Neg. |
| 8,8'-{{5-[3-(α,α,α-trifluoro-m-tolyl)ureido]-1,3-phenylene}bis(cabonylimino)}di-1,3,6-naphthalenetrisulfonic acid, hexasodium salt | +5 | +1 |
| 8,8'-{{5-[3-(3-nitro-p-tolyl)ureido]-1,3-phenylene}bis(carbonylimino)}di-1,3,6-naphthalenetrisulfonic acid, hexasodium salt | +5 | +1 |
| 8,8'-{{5-{3-[m-(fluorosulfonyl)phenyl]-ureido}1,3-phenylene}bis(carbonylimino)}di-1,3,6-naphthalenesulfonic acid, hexasodium salt | +6 | +1 |

*Tests identified by code herein.
**4 = Activity 4 wells, a serial dilution assay; higher well number indicates higher activity. The serial dilutions are two-fold.

We claim:

1. A compound selected from those of the formula:

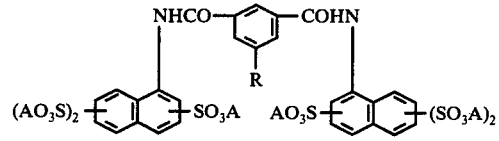

wherein R is $NO_2$ or $NH_2$; and A is hydrogen, alkali metal or alkaline earth, with the proviso that each A is identical in the same compound.

2. A compound selected from those of the formula:

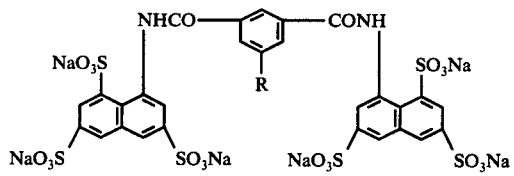

wherein R is $-NO_2$ or $-NH_2$.

3. A compound selected from those of the formula:

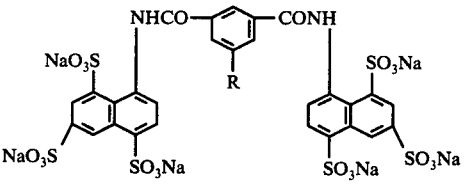

wherein R is $NO_2$ or $NH_2$.

4. A compound according to claim 2, 8,8'-[(5-nitro-1,3-phenylene)bis(carbonylimino)]-di-1,3,6-naphthalenetrisulfonic acid, hexasodium salt.

5. A compound according to claim 2, 8,8'-[(5-amino-m-phenylene)bis(carbonylimino)]di-1,3,6-naphthalenetrisulfonic acid, hexasodium salt.

6. A compound according to claim 3, 8,8'-[(5-nitro-1,3-phenylene)bis(carbonylimino)]-1,3,5-naphthalenetrisulfonic acid, hexasodium salt.

7. A compound according to claim 3, 8,8'-[(5-amino-m-phenylene)bis(carbonylimino)]di-1,3,5-naphthalenetrisulfonic acid, hexasodium salt.

* * * * *